(12) United States Patent
Saenz Villalobos et al.

(10) Patent No.: US 11,129,623 B2
(45) Date of Patent: Sep. 28, 2021

(54) DUAL SUPPORT JAW DESIGN

(71) Applicant: BOSTON SCIENTIFIC SCIMED, INC., Maple Grove, MN (US)

(72) Inventors: Gonzalo Jose Saenz Villalobos, Heredia (CR); Daniel Congdon, Pepperell, MA (US); Martin Hynes, Knocknacarra (IE); Daniel Calvo Camacho, Ciudada Colon (CR); Diana Catalina Rodriguez Forero, San Jose (CR)

(73) Assignee: Boston Scientific Scimed, Inc., Maple Grove, MN (US)

( * ) Notice: Subject to any disclaimer, the term of this patent is extended or adjusted under 35 U.S.C. 154(b) by 109 days.

(21) Appl. No.: 16/248,306

(22) Filed: Jan. 15, 2019

(65) Prior Publication Data

US 2019/0223875 A1 Jul. 25, 2019

Related U.S. Application Data

(60) Provisional application No. 62/621,815, filed on Jan. 25, 2018.

(51) Int. Cl.
*A61B 17/122* (2006.01)
*A61B 17/08* (2006.01)
(Continued)

(52) U.S. Cl.
CPC .......... *A61B 17/122* (2013.01); *A61B 17/083* (2013.01); *A61B 17/1285* (2013.01);
(Continued)

(58) Field of Classification Search
CPC . A61B 17/122; A61B 17/128; A61B 17/1285; A61B 2017/2936
See application file for complete search history.

(56) References Cited

U.S. PATENT DOCUMENTS 9,271,737 B2 3/2016 Castro et al.
9,339,270 B2 * 5/2016 Martinez ................ A61B 17/08
(Continued)

FOREIGN PATENT DOCUMENTS

CN 102626335 B 4/2014
CN 206714786 U 12/2017
(Continued)

*Primary Examiner* — Katrina M Stransky
*Assistant Examiner* — Mohammed S Adam
(74) *Attorney, Agent, or Firm* — Fay Kaplun & Marcin, LLP

(57) ABSTRACT

A device for treating tissue including a capsule including a channel extending therethrough; clip arms extending from a proximal end to a distal end, proximal ends received within the channel to be moved between a tissue receiving configuration, in which distal ends of the arms are separated, and a tissue clipping configuration, in which distal ends of the arms are moved toward one another, the arms including proximal and distal portions, the proximal portion including longitudinal legs extending from the proximal end to the distal portion, a plane of the legs being rotated about a longitudinal axis of the arms from a plane including the distal portion; and a yoke including proximal and distal portions, the distal portion being releasably coupled to the clip legs via a pin, the pin is inserted through the distal portion.

15 Claims, 4 Drawing Sheets

(51) Int. Cl.
*A61B 17/128* (2006.01)
*A61B 17/12* (2006.01)
*A61B 17/00* (2006.01)
*A61B 17/29* (2006.01)

(52) U.S. Cl.
CPC .......... *A61B 2017/00473* (2013.01); *A61B 2017/12004* (2013.01); *A61B 2017/2936* (2013.01)

(56) References Cited

U.S. PATENT DOCUMENTS

| | | | |
|---|---|---|---|
| 2002/0078967 | A1 | 6/2002 | Sixto, Jr. et al. |
| 2010/0152753 | A1* | 6/2010 | Menn .................. A61B 17/10 606/158 |
| 2012/0165863 | A1* | 6/2012 | McLawhorn .......... A61B 17/29 606/207 |
| 2013/0289586 | A1* | 10/2013 | Mazzucco ............ A61B 17/083 606/151 |
| 2014/0249553 | A1 | 9/2014 | Kimura et al. |

FOREIGN PATENT DOCUMENTS

| | | |
|---|---|---|
| EP | 2 591 736 | 5/2013 |
| WO | 2017/066987 | 4/2017 |

* cited by examiner

DUAL SUPPORT JAW DESIGN

PRIORITY CLAIM

The present disclosure claims priority to U.S. Provisional Patent Application Ser. No. 62/621,815 filed Jan. 25, 2018; the disclosure of which is incorporated herewith by reference.

FIELD OF THE INVENTION

The present disclosure relates to compression clips, and more specifically, to compression clips delivered to a target site within the body through a delivery device such as an endoscope to cause hemostasis of blood vessels located along the gastrointestinal tract.

BACKGROUND

Pathologies of the gastrointestinal (GI) system, including the esophageal tract, stomach, biliary tree, duodenal tract, colonic tract and associated anatomies are often treated through endoscopic procedures, many of which require active and/or prophylactic hemostasis to control internal bleeding. Catheter-based minimally invasive devices for deploying hemostatic clips via endoscopes are often used to stop internal bleeding by clamping together the edges of wounds or incisions. Hemostasis clips grab tissue surrounding a wound and hold edges of the wound together to allow natural healing processes to close the wound. Specialized endoscopic clipping devices are used to deliver the clips to desired locations within the body and to position and deploy the clips in the desired locations within the body after which the clip delivery device is withdrawn, leaving the clip(s) in place within the body. Typical procedures involve more than one clip to close larger injured areas.

Hemostatic clips often involve a capsule which contains a portion of the length of the jaws after deployment, and a deployment mechanism that pulls and pushes the clip arms in and out of the capsule to open and close the clip arms. Such hemostasis clips include a pair of arms that act as jaws and which are constructed, for example, from a metal sheet which is formed to the shape each arm. Many of the arms are relatively flat and may exhibit reduced strength in the open position, making them easy to deform beyond their desired open position. Thus, there is a need for stronger clip arms with a reduced risk of plastic deformation, especially in longer clip arms.

SUMMARY

The present disclosure relates to a device for treating tissue. The device includes a capsule extending longitudinally from a proximal end to a distal end and including a channel extending therethrough, clip arms extending from a proximal end to a distal end, proximal ends received within a channel of a capsule to be moved between a tissue receiving configuration, in which distal ends of the clip arms are separated from one another, and a tissue clipping configuration, in which distal ends of the clip arms are moved toward one another, the clip arms including a proximal portion and a distal portion, the proximal portion including a pair of longitudinal legs extending from the proximal end to the distal portion, a plane of the legs being rotated about a longitudinal axis of the clip arms from a plane including the distal portion and a yoke including a proximal portion configured to be connected to a control member and a distal portion, the distal portion being releasably coupled to the clip legs via pin, the pin configured to be inserted through the distal portion in a direction perpendicular to the longitudinal axis of the yoke.

In an embodiment, the legs are rotated 90 degrees relative to the distal portion.

In an embodiment, the distal portion of the yoke includes a pair of arms, each arm having two distal opposed portions, the opposed portion defining a pin receiving space configured to releasably receive the pin.

In an embodiment, capsule includes a bar extending across a distal end of the channel between the clip arms so that, as the clip arms are moved proximally out of the channel, a curvature of the clip arms slides along the bar, forcing them into the tissue receiving configuration.

In an embodiment, a first one of the legs of each clip arm includes a locking mechanism configured to engage locking features on the capsule when the clip arms are released from the yoke.

In an embodiment, the locking mechanism is a tab.

In an embodiment, the locking features are windows.

In an embodiment, the legs include slots at proximal ends thereof configured to receive the pin therethrough to releasably couple the clip arms to the yoke.

In an embodiment, the proximal ends of the legs are configured to be received between the arms of the yoke.

The present disclosure also relates to a clipping device. The device includes a proximal portion including a control member extending from a proximal end to a distal end and a yoke and a distal portion releasably coupled to the proximal portion so that the distal portion is deployable therefrom, the distal portion including: a capsule extending longitudinally from a proximal end to a distal end and including a channel extending therethrough; and clip arms extending from a proximal end to a distal end, proximal ends received within a channel of a capsule to be moved between a tissue receiving configuration, in which distal ends of the clip arms are separated from one another, and a tissue clipping configuration, in which distal ends of the clip arms are moved toward one another, the clip arms including a proximal portion and a distal portion, the proximal portion including a pair of longitudinal legs extending from the proximal end to the distal portion, a plane of the legs being rotated about a longitudinal axis of the clip arms from a plane including the distal portion, wherein, the yoke includes a proximal portion configured to be connected to the control member and a distal portion, the distal portion being releasably coupled to the clip legs via pin.

In an embodiment, the legs are rotated 90 degrees relative to the distal portion.

In an embodiment, the distal portion of the yoke includes a pair of arms, each arm having two distal opposed portions, the opposed portion defining a pin receiving space configured to releasably receive the pin a direction perpendicular to a longitudinal axis of the device.

In an embodiment, the legs include slots at proximal ends thereof configured to receive the pin therethrough to releasably couple the clip arms to the yoke.

In an embodiment, the opposed portions are separated at a distal end by a slot open to the pin receiving space, the slot having a cross-sectional area that is smaller than a cross-sectional area of the pin so that once the pin is moved through the slot into the pin receiving space, the pin is releasably locked therein.

In an embodiment, a first one of the legs of each clip arm includes a locking mechanism configured to engage locking features on the capsule when the clip arms are released from the yoke.

DETAILED DESCRIPTION

Figure 1:
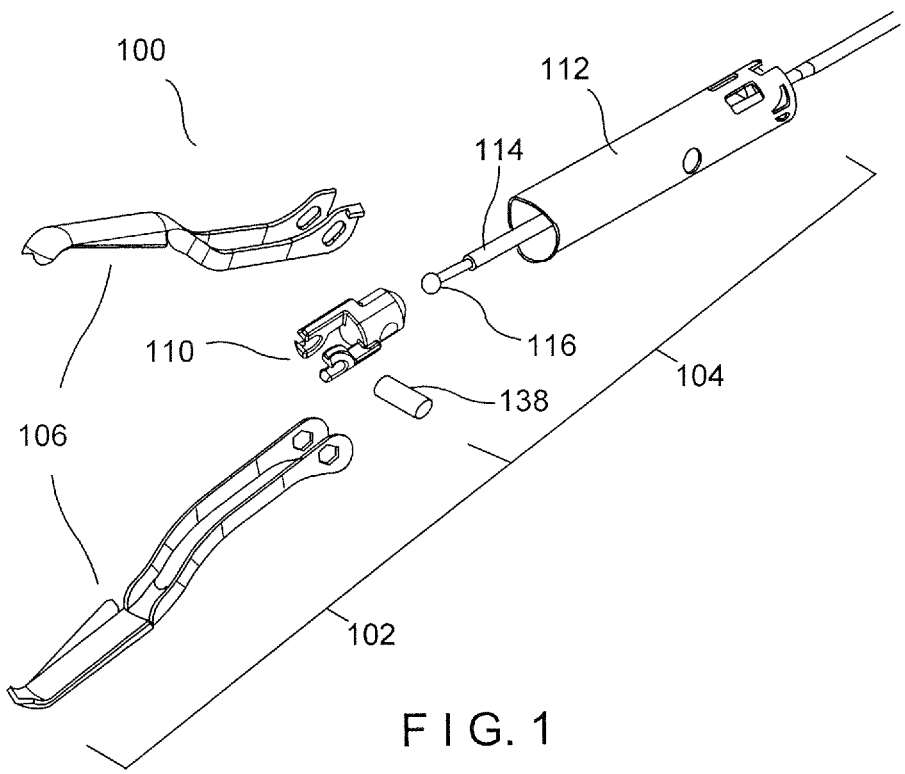
FIG. 1 shows a perspective view of a system according to an exemplary embodiment of the present disclosure.

The present disclosure may be further understood with reference to the following description and the appended drawings, wherein like elements are referred to with the same reference numerals. The present disclosure relates to endoscopic clipping systems for treating tissue perforations, defects and/or bleeds. Exemplary embodiments of the present disclosure describe a clip assembly including a pair of clip arms with each of the arms having two legs extending proximally and oriented parallel to a plane within which the clip arms rotate between the open and closed positions. This arrangement strengthens the clip arms to reduce the risk of plastic deformation of the arms as they are opened. Furthermore, stronger clip arms prevent over-bending that could result in premature deployment in force-based designs. For example, over-bent clip arms require more force to pull the deformed arms proximally into the capsule. This force required may exceed the threshold of the tension/force-based deployment mechanism, causing the deployment mechanism to break before the arms are pulled in. It should be noted that the terms "proximal" and "distal," as used herein, are intended to refer to toward (proximal) and away from (distal) a user of the device.

Figure 2:
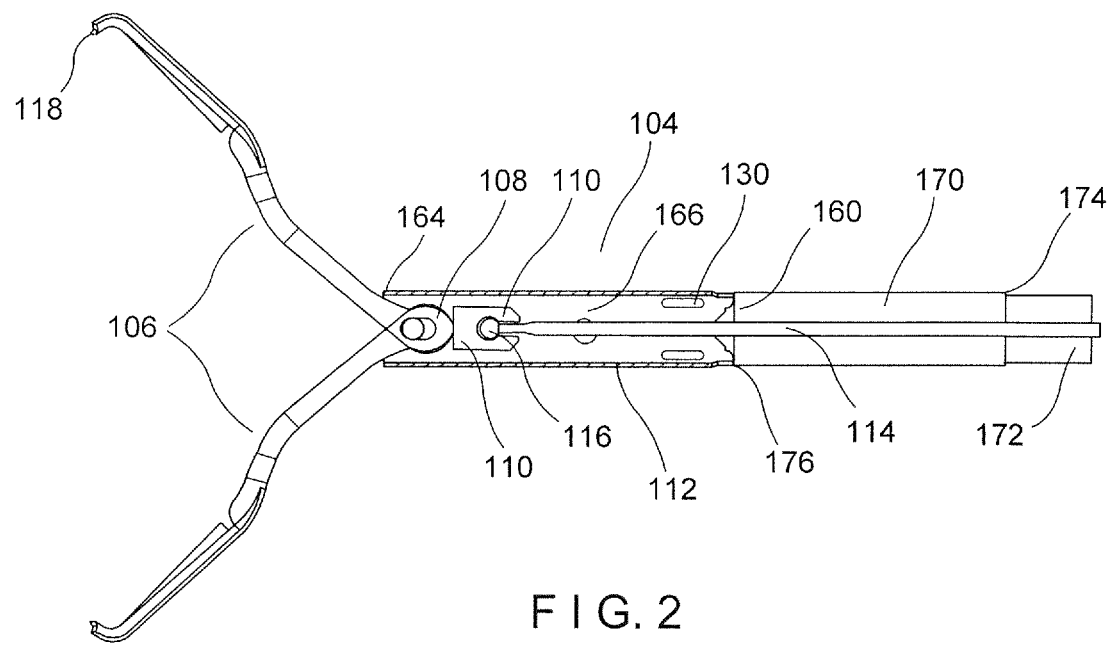
FIG. 2 shows a longitudinal cross-sectional side view of a clip assembly of the system of FIG. 1.

As shown in FIGS. 1-2, a clip assembly 100 according to an exemplary embodiment of the present disclosure comprises a clip 102 insertable into a living body through, for example, a working channel of an endoscope to access target tissue to be treated. As would be understood by those skilled in the art, the clip assembly 100 is sufficiently flexible to permit it to traverse a tortuous path through the body—e.g., passing through the working channel of an endoscope inserted through a natural body lumen accessed via a natural bodily orifice. The clip 102 includes clip arms 106, proximal ends 108 of which are coupled to a yoke 110 slidably received within a capsule 112 so that the clip arms 106 are rotatable between an open tissue receiving configuration and a closed tissue clipping configuration. The yoke 110 is configured to be coupled to the distal end 116 of a control member 114. For example, an enlarged distal end 116 of the control member 114 may be received within a cavity in the yoke 110 sized to prevent the distal end from being pulled proximally out of the yoke 110. The control member 114 is slidably received within an insertion device 104 so that longitudinal movement of the control member 114 relative to the capsule 112 moves the clip arms 106 between the tissue receiving and tissue clipping configurations. Each of the clip arms 106, in this embodiment, includes a proximal portion 122 having two legs 126 which are rotated 90 degrees from a distal head portion 120 of the clip arms 106 so that they extend substantially within a plane within which the arms 106 rotate between the open and closed configurations. The configuration of the legs 126 strengthens the clip arms 106 to enhance their resistance to plastic deformation during clipping. The clip 102 is releasably coupled to the insertion device 104 of the clip assembly 100 by any known mechanism for permitting the clip to be locked in position clipped to target tissue while the insertion device 104 is removed from the body. As would be understood by those skilled in the art, the apparatus further includes a handle (not shown) that remains outside the body accessible to the user when the insertion device 104 is inserted into the body to deploy the clip 102.

In use, once the clip assembly 100 has been used to clip a portion of target tissue, the control member 114 is drawn proximally relative to the capsule 112 until a predetermined threshold force is exceeded, releasing the yoke 110 from the capsule 112 to deploy the clip 102 in the body as will be described in more detail below.

Figure 3:
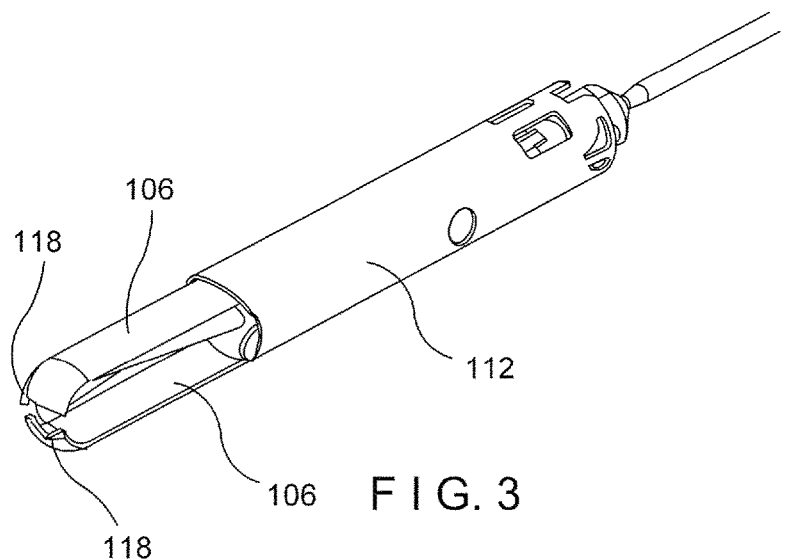
FIG. 3 shows an enlarged perspective view of a portion of the clip assembly of the system of FIG. 1.

As described above, the clip 102 includes a pair of clip arms 106, the proximal ends 108 of which are coupled to the yoke 110 which is slidably received within the capsule 112. Each of the clip arms 106 extends between a proximal end 108 connected to the yoke 110 and a distal end 118. As those skilled in the art will understand, the clip arms 106 of this embodiment are movable toward an open tissue receiving configuration via a bar 161 at a distal end of the capsule 112, as will be described in further detail below. Specifically, the clip arms 106 have a curvature that, when the clip arms 106 are slid distally out of the capsule 112, forces the clip arms 106 to the open, tissue receiving configuration. In the tissue receiving configuration shown in FIG. 2, the distal ends 118 of the clip arms 106 are spread apart from one another to receive tissue therebetween. When the clip arms 106 are drawn into the capsule 112, the capsule 112 constrains the clip arms 106, drawing the distal ends 118 thereof together and holding them in the tissue clipping configuration, as depicted in FIG. 3.

Figure 4:
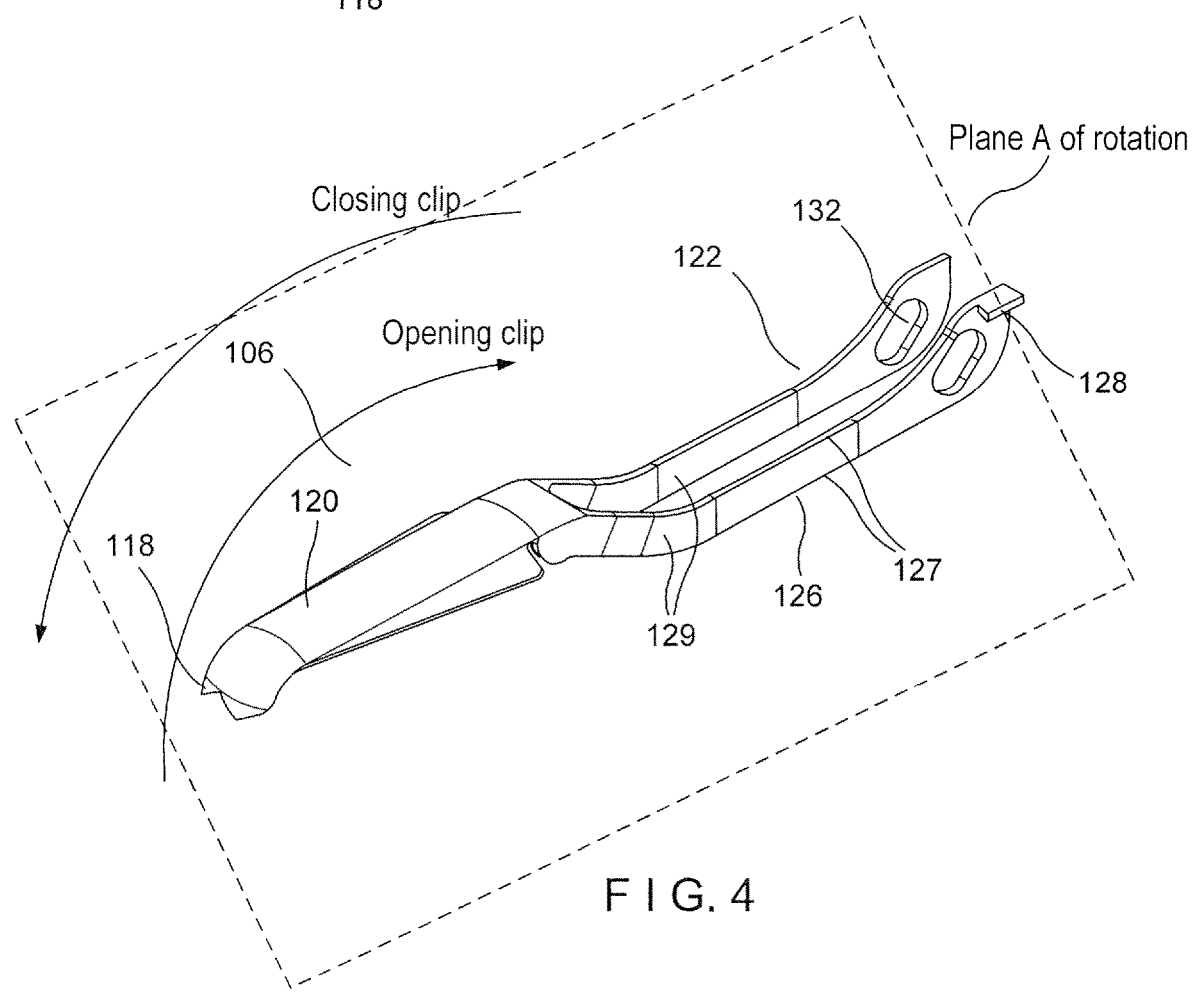
FIG. 4 shows an enlarged perspective view of a clip arm of the clip assembly of the system of FIG. 1.
Figure 5:
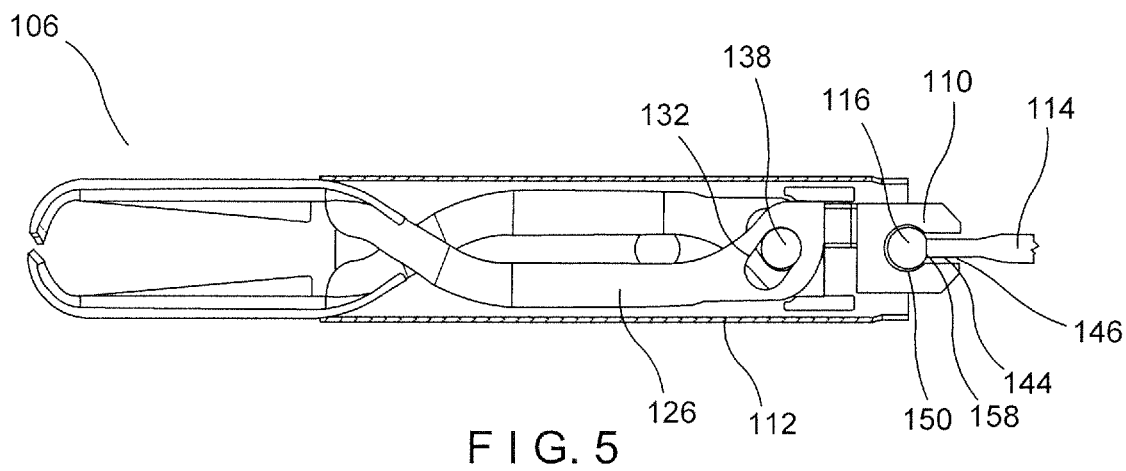
FIG. 5 shows an enlarged cross-sectional view of a portion of the clip assembly of the system of FIG. 1 in a plane within which the clip arms rotate between the tissue receiving and tissue clipping configurations.

According to an exemplary embodiment shown in FIG. 4, each of the clip arms 106 includes a distal head portion 120 and a proximal leg portion 122. The head portion 120 is formed similarly to current "flat" designs with a tissue gripping distal end 118 and a curved head portion 120 extending from the leg portion 122 to the distal end 118. The leg portion 122 in this embodiment includes two legs 126 parallel to one another and aligned with the lateral edges of the head portion 120. The legs 126 are also substantially flat and can be any length desired depending on the procedure and the desired dimensions of the clip. However, a plane of each leg 126 is rotated 90 degrees about an axis parallel to a central longitudinal axis of the clip arms from a plane of the head portion 120, as shown in FIG. 5 so that the legs 126 are substantially parallel to a plane, A, within which the alias 106 rotate between the open and closed configurations with a thickness 127 (i.e., a thickness perpendicular to the plane of rotation of the arms 106) that is smaller than a width of connecting sides 129 (i.e., parallel to the plane of rotation of the arms 106), increasing the amount of force bending force that the legs 126 can resist without plastic deformation. That is, because the legs 126 have a greater extent in the direction along which bending forces are applied (i.e., in the plane of rotation of the arms 106) the legs 126 can resist higher forces than would be the case if the legs 126 were rotated 90 degrees, compared to this design, about an axis parallel to a central longitudinal axis of the clip arms to have a smaller extent in the direction along which bending forces are applied.

Figure 8:
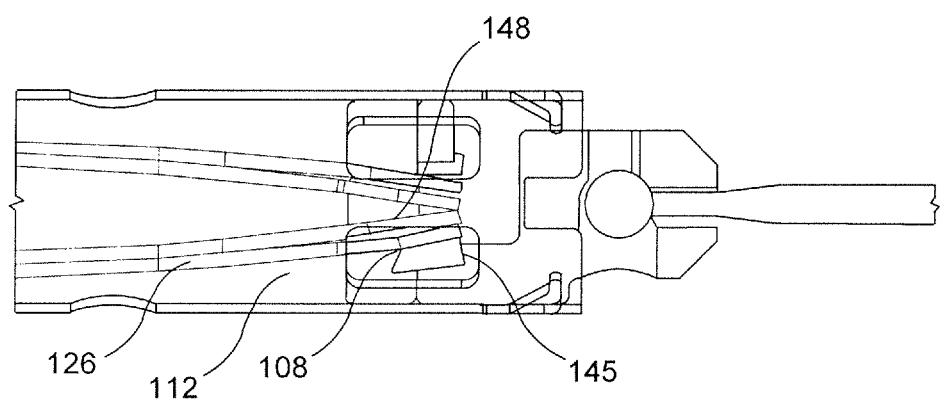
FIG. 8 shows an enlarged, partially transparent, side view of a portion of the clip assembly of the system of FIG. 1.

As would be understood by those skilled in the art, the clip arms 106 may include optional gripping features configured to facilitate the gripping of tissue therebetween. For example, distal ends 118 of the clip arms 106 may include tips extending laterally inward toward one another and/or teeth, protrusions, spikes or other structures configured to grip tissue between the distal ends 118 of the clip arms 106. One or both of the clip arms 106 may also include a locking feature configured to lock the clip arms 106 in the tissue gripping configuration after target tissue has been gripped via the clip arms 106. In one embodiment, at least one of the legs 126 of the clip arms 106 includes a locking tab 128 extending laterally outward therefrom. This locking tab 128 is configured to engage a portion of the capsule 112 when the clip arms 106 have been released from the yoke 110, as can be seen in FIG. 8. For example, while the yoke is still connected to the clip 102, the locking tab 128 may be constrained against its natural bias to a position separated from the wall of the capsule 112. But, when the clip arms 106 are fully drawn into the capsule 112 and the yoke 110 has been released from the clip 102 as will be described in more detail below, the locking tab 128 is released to spring laterally outward to project through and engage a depression or locking windows 130 formed in a wall of the capsule 112 to lock the clip arms 106 relative to the capsule 112 in the tissue gripping configuration, as will described in greater detail below.

Figure 7:
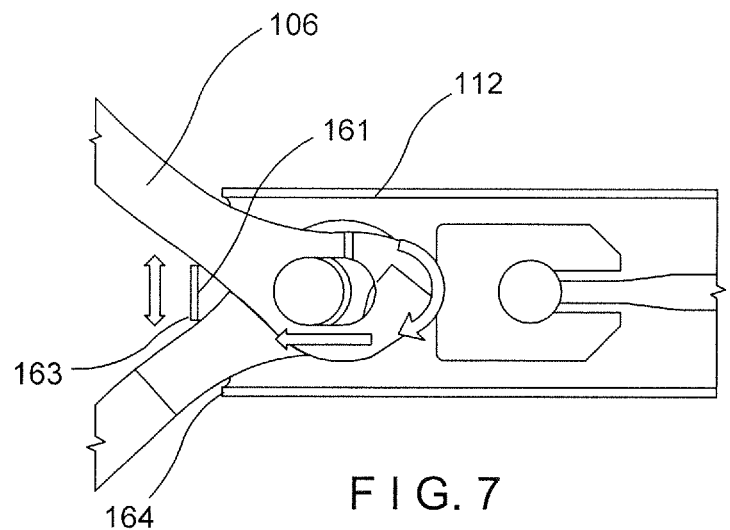
FIG. 7 shows an enlarged, partially transparent, side view of a portion of the clip assembly of the system of FIG. 1.

A proximal portion of each of the legs 126 (e.g., distal of the locking tabs at the proximal ends 118) may include a slot 132 sized and shaped to receive therein a pin 138 of the yoke 110 so that the clip arms 106 are engaged and aligned with the yoke 110, as can be seen in FIG. 5. Thus, moving the yoke 110 relative to the capsule 112 correspondingly moves the clip arms 106 relative to the capsule 112 so that the clip arms 106 may be moved between the tissue receiving and tissue gripping configurations via movement of the yoke 110. The slot 132 may be formed as a substantially oval slot that allows for rotation of the legs 126 when moving between the tissue receiving and tissue gripping configurations. Specifically, each of the oval slots 132 are angled away from a longitudinal axis parallel to the longitudinal axis of the device when the clip arms 106 are in the closed configuration, as shown in FIG. 5. The oval slots 132 are angled in opposing directions with the slot 132 of the bottom arm 106 angled upward and the slot 132 of the upper arm angled downward in the tissue gripping configuration. As the clip arms 106 rotate to the open tissue receiving configuration, the slots 132 rotate about the pin 138 so that they are parallel to one another and the pin 138 is positioned at a distal end of both of the slots 132, as shown in FIG. 7.

Figure 6:
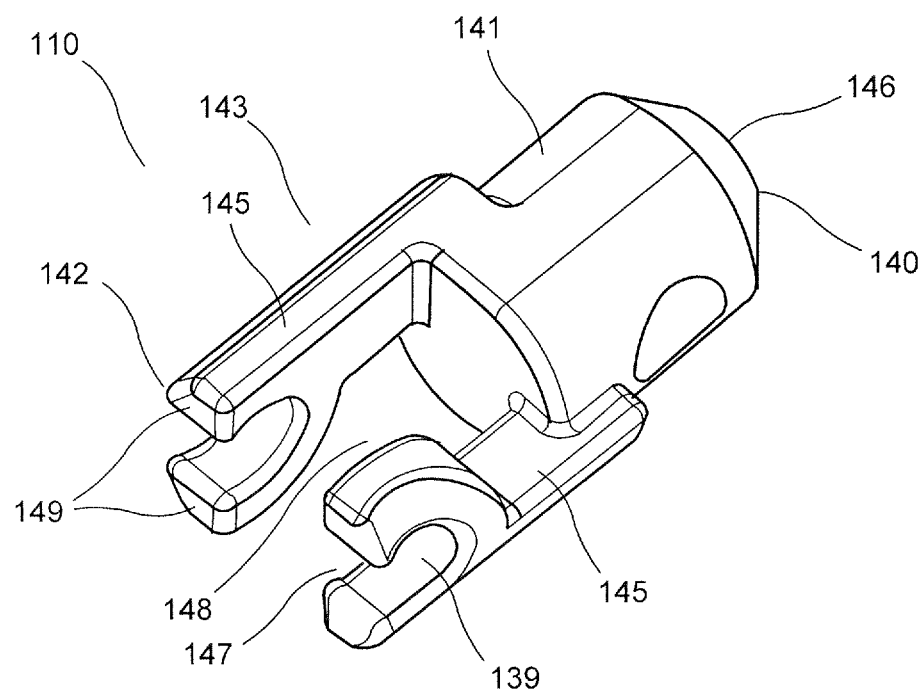
FIG. 6 shows an enlarged perspective view of a yolk of the clip assembly of the system of FIG. 1.

The yoke 110, shown in FIG. 6, extends longitudinally from a proximal end 140 to a distal end 142 and includes a proximal portion 141 configured to be connected to the enlarged distal end 116 of the control member 114 and a distal portion 143 configured to be connected to the clip arms 106. The distal portion 143 comprises a pair of distally extending arms 145 with two distal opposed portions 149 configured to receive a pin 138 of the clip 102 that pass through proximal openings in the clip arms 106. The opposed portions 149 are separated at a distal end by a slot 147 open to a pin receiving space 139 extending between the opposed portions 149. The distal slots 147 have a cross-sectional area (e.g., width) smaller than the cross-sectional area of the pin 138 with opposed portions 149 of the arms 145 configured to slidably receive the pin 138 within the pin receiving spaces 139. In an exemplary embodiment, the opposed portions 149 may be biased toward one another so that, once the pin 138 is moved into the slots 147, the opposed portions 149 spring back to lock the pin within the pin receiving spaces 139. The pin 138, in this embodiment, extends in a direction substantially perpendicular to a longitudinal axis of the clip 102 and is substantially cylindrical. However, those skilled in the art will understand that the pin 138 may have any cross-sectional shape so long as it is sized to be releasably locked within the pin-receiving spaces 139. The arms 145 are positioned at lateral sides of the yoke 110 to form a clip receiving space 148 therebetween for receiving proximal ends 108 of the clip legs 126, as shown in FIG. 8. Specifically, proximal ends of the clip legs 126 are slightly bent to fit inside the clip receiving space 148 between the yoke arms 145 to prevent the locking tabs 128 from engaging the capsule 112. The yoke 110 further includes a longitudinal slot 144, as seen in FIG. 5, extending from a proximal opening 146 at the proximal end 140 of the yoke 110 to a distal portion 150 which is sized and shaped to receive the enlarged end 116 of the control member 114. In an exemplary embodiment, the enlarged distal end 114 may be configured as a ball received within a correspondingly sized and shaped socket of the distal portion 150. In an embodiment, a proximal portion of the slot 144 may taper from the proximal opening 146 to a narrow opening 158 of the distal portion 150. The narrow opening 158 has a cross-sectional area (e.g., diameter) smaller than a cross-sectional area of the distal portion 150 of the slot 144 so that the enlarged end 116 is locked within the distal portion 150, coupling the control member 114 to the yoke 110. Thus, longitudinal movement of the control member 114 relative to the capsule 112 controls movement of the clip arms 106 between the tissue receiving and tissue clipping configurations.

Turning back to FIG. 2, the capsule 112 extends longitudinally from a proximal end 160 to a distal end 164 and includes a channel 166 extending longitudinally therethrough. The channel 166 is sized and shaped to receive therein the yoke 110 and at least proximal portions of the clip arms 106. As described above, the capsule 112 includes a tab or bar 161 at the distal end 164. The bar 161 extends across a distal opening 163 of the capsule 112 from a first lateral wall to a second opposing wall. As shown in FIG. 7, the bar 161 extends through a space between the clip arms 106. Thus, as the arms are pushed distally out of the capsule 112, inner surfaces of the curvature of the clip arms 106 slide against the bar 161, forcing the clip arms 106 toward the tissue receiving configuration. As described above, the capsule 112 includes locking features 130 (e.g., locking windows) for engaging locking tabs 128 of the legs 126 after the clip 102 has been deployed. In one embodiment, the capsule 112 includes a pair of diametrically opposed windows 130 for engaging the legs. In another embodiment, the pair of opposed windows 130 may be positioned within a first half of the circumference of the capsule 112. It will be understood by those of skill in the art, however, that the capsule 112 may include any number of features such as recesses or windows for receiving any number of corresponding engaging features of the clip arms/legs 106.

The clipping assembly in this embodiment includes a catheter 170, a flexible member 172 extending proximally therefrom, and a control member 114 extending longitudinally through the flexible member 172 and the catheter 170. A proximal end of the flexible member 172 in this embodiment is connected to a handle portion as described above. The catheter 170 extends longitudinally from a proximal end 174 connected to the flexible member 172 to a distal end 176 configured to be releasably coupled to the capsule 112. The catheter 170 includes engaging features at a distal end thereof that engage with engaging features of the capsule 112. For example, in one embodiment, the engaging features may be configured as tabs extending laterally outward (e.g. extending away from a longitudinal axis of the catheter 170) from the distal end 176. The tabs of the engaging features may be sized and shaped to correspond to, for example, grooves at the proximal end of the capsule so that the tabs may be received within the groove via a snap fit. The control member 114 extends through the catheter 170 and flexible member 172 from the enlarged distal end 116 to a proximal end connected to the actuator of the handle portion. The flexible member 172 may be formed as a coil or wire having sufficient flexibility to be passed through even tortuous paths of the living body and, in this embodiment, is size and shaped to be pass through a working channel of an endoscope or other insertion device. The flexible member 172, however, may be formed of any other suitable flexible structure so long as the flexible member 172 is capable of providing a force compression sufficient to counter the tension to be place on the control member 114 from the clip assembly 102.

The exemplary embodiments describe and show a capsule 112 which abuts a catheter 170 when the clip assembly is moved from the tissue receiving to the tissue gripping configuration so that breakage/detachment of the yoke 110 from the pin 138 deploys the clip 102. It will be understood by those of skill in the art, however, that the capsule 112 and the catheter 170 may be releasably coupled to one another in any of a variety of ways. For example, in some embodiments, the capsule 112 may be released from the catheter 170 via breakage/detachment of the enlarged distal end 116 from a remaining portion of the control member 114, deploying the clip 102.

In use, the clip 102 is inserted through the working channel of an endoscope (or any other insertion device) and inserted into the body (e.g., through a natural body lumen) to a site adjacent to a target portion of tissue to be clipped. The clip 102 is inserted to the target tissue in the insertion configuration to facilitate its passage through the working channel. Upon reaching the site of the target tissue, the clip 102 is advanced out of the distal end of the working channel and the clip arms 106 are extended out of the capsule 112 to move the clip arms 106 to the tissue receiving configuration. Once the target tissue has been received between the clip arms 106, the clip assembly 102 may be moved toward the tissue gripping configuration so that the target tissue is gripped between the distal ends 118 thereof. The clip arms 106 are moved toward the tissue gripping configuration by drawing the control member 114 proximally relative to the capsule 112. Once the clip assembly 102 is in the tissue gripping configuration, the control member 114 may be drawn further proximally to lock the clip arms 106 with respect to the capsule 112 and deploy the clip 102, as described below.

Figure 9:
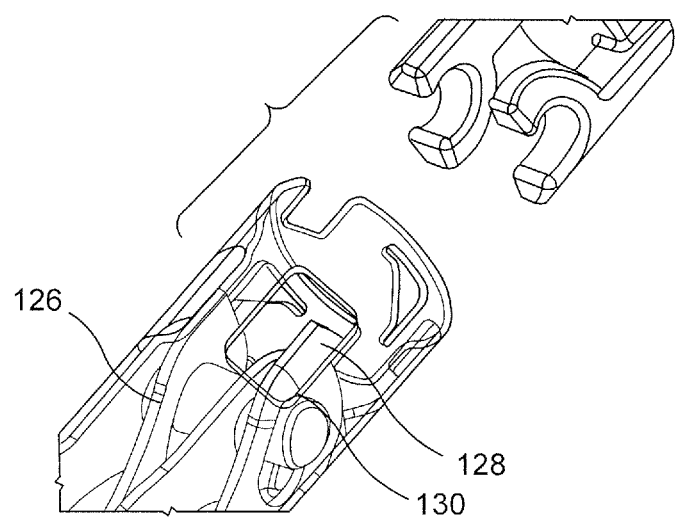
FIG. 9 shows and enlarged, partially transparent, perspective view of a portion of a capsule and a yolk of the clip assembly of the system of FIG. 1.

To deploy the clip assembly 102, the control member 114 is drawn further proximally until the connection between the yoke 110 and the pin 138 is broken. Specifically, when the control member 114 exerts a proximal force on the yoke 110 greater than a predetermined threshold value, the opposed portions 149 yield, separating the yoke 110 from the pin 138. The disengagement of the yoke 110 from the pin 138 releases the proximal ends of the legs 126, which are free to move radially away from the central axis so that the locking tabs 128 engage the windows 130 in the capsule 112, as depicted in FIG. 9. This engagement works as a locking mechanism which prevents the clip arms from disengaging from the capsule 112 when the clip 102 is in position. The control member 114 is drawn proximally until the catheter 170 is entirely disconnected from the capsule 112, releasing the clip 102. The catheter 170, yoke 110 and control member 114 may then all be removed from the body.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A device for treating tissue, comprising:
   a capsule extending longitudinally from a proximal end to a distal end and including a channel extending therethrough;
   clip arms extending from a proximal end to a distal end, proximal ends received within the channel of the capsule to be moved between a tissue receiving configuration, in which distal ends of the clip arms are separated from one another, and a tissue clipping configuration, in which distal ends of the clip arms are moved toward one another, the clip arms including a proximal portion and a distal portion, the proximal portion including a pair of longitudinal legs extending from the proximal end to the distal portion, a plane of the legs being rotated about a longitudinal axis of the clip arms from a plane including the distal portion; and
   a yoke including a proximal portion configured to be connected to a control member and a distal portion, the distal portion being releasably coupled to the clip arms via a pin, the pin configured to be inserted through the distal portion in a direction perpendicular to the longitudinal axis of the yoke.

2. The device of claim 1, wherein the legs are rotated 90 degrees relative to the distal portion.

3. The device of claim 1, wherein the distal portion of the yoke includes a pair of arms, each arm having two distal opposed portions, the opposed portions defining a pin receiving space configured to releasably receive the pin.

4. The device of claim 3, wherein the capsule includes a bar extending across a distal end of the channel between the clip arms so that, as the clip arms are moved proximally out of the channel, a curvature of the clip arms slides along the bar, forcing them into the tissue receiving configuration.

5. The device of claim 1, wherein one of the legs of each clip arm includes a locking mechanism configured to engage locking features on the capsule when the clip at ins are released from the yoke.

6. The device of claim 5, wherein the locking mechanism is a tab.

7. The device of claim 5, wherein the locking features are windows.

8. The device of claim 1, wherein the legs include slots at proximal ends thereof configured to receive the pin therethrough to releasably couple the clip arms to the yoke.

9. The device of claim 8, wherein the proximal ends of the legs are configured to be received between the arms of the yoke.

10. A clipping device, comprising:
a proximal portion including a control member extending from a proximal end to a distal end and a yoke; and
a distal portion releasably coupled to the proximal portion so that the distal portion is deployable therefrom, the distal portion including:
a capsule extending longitudinally from a proximal end to a distal end and including a channel extending therethrough; and
clip arms extending from a proximal end to a distal end, proximal ends received within the channel of the capsule to be moved between a tissue receiving configuration, in which distal ends of the clip arms are separated from one another, and a tissue clipping configuration, in which distal ends of the clip arms are moved toward one another, the clip arms including a proximal portion and a distal portion, the proximal portion including a pair of longitudinal legs extending from the proximal end to the distal portion, a plane of the legs being rotated about a longitudinal axis of the clip arms from a plane including the distal portion,
wherein, the yoke includes a proximal portion configured to be connected to the control member and a distal portion, the distal portion being releasably coupled to the clip arms via a pin.

11. The device of claim 10, wherein the legs are rotated 90 degrees relative to the distal portion.

12. The device of claim 10, wherein the distal portion of the yoke includes a pair of arms, each arm having two distal opposed portions, the opposed portions defining a pin receiving space configured to releasably receive the pin a direction perpendicular to a longitudinal axis of the device.

13. The device of claim 10, wherein the legs include slots at proximal ends thereof configured to receive the pin therethrough to releasably couple the clip arms to the yoke.

14. The device of claim 12, wherein the opposed portions are separated at a distal end by a slot open to the pin receiving space, the slot having a cross-sectional area that is smaller than a cross-sectional area of the pin so that once the pin is moved through the slot into the pin receiving space, the pin is releasably locked therein.

15. The device of claim 10, wherein a first one of the legs of each clip arm includes a locking mechanism configured to engage locking features on the capsule when the clip arms are released from the yoke.

* * * * *